(12) United States Patent
Crum et al.

(10) Patent No.: US 12,220,393 B2
(45) Date of Patent: Feb. 11, 2025

(54) COMPOSITIONS AND METHODS FOR THE TREATMENT OF ZIKA VIRAL DISEASES

(71) Applicants: The ProImmune Company LLC, Rhinebeck, NY (US); Georgia State University Research Foundation, Atlanta, GA (US)

(72) Inventors: Albert Crum, Rhinebeck, NY (US); Julia Hilliard, Atlanta, GA (US)

(73) Assignees: ProImmune Company LLC, Rhinebeck, NY (US); Georgia State University Research Foundation, Atlanta, GA (US)

( * ) Notice: Subject to any disclaimer, the term of this patent is extended or adjusted under 35 U.S.C. 154(b) by 787 days.

(21) Appl. No.: 16/610,488

(22) PCT Filed: May 1, 2018

(86) PCT No.: PCT/US2018/030500
§ 371 (c)(1),
(2) Date: Nov. 1, 2019

(87) PCT Pub. No.: WO2018/204394
PCT Pub. Date: Aug. 11, 2018

(65) Prior Publication Data
US 2020/0155492 A1     May 21, 2020

Related U.S. Application Data

(60) Provisional application No. 62/500,430, filed on May 2, 2017.

(51) Int. Cl.
| | | |
|---|---|---|
| *A61K 31/198* | (2006.01) | |
| *A61K 33/04* | (2006.01) | |
| *A61P 31/14* | (2006.01) | |
| *B82Y 5/00* | (2011.01) | |

(52) U.S. Cl.
CPC ............ *A61K 31/198* (2013.01); *A61K 33/04* (2013.01); *A61P 31/14* (2018.01); *B82Y 5/00* (2013.01)

(58) Field of Classification Search
None
See application file for complete search history.

(56) References Cited

U.S. PATENT DOCUMENTS

| | | |
|---|---|---|
| 6,013,632 A | 1/2000 | Jones et al. |
| 2016/0101079 A1 | 4/2016 | Crum |

FOREIGN PATENT DOCUMENTS

| | | |
|---|---|---|
| WO | 2016/033183 A1 | 3/2016 |

OTHER PUBLICATIONS

Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
International Search Report and Written Opinion for Application No. PCT/US2018/030500, mailed Nov. 8, 2018.
Laughhunn A. et al., "Amustaline (S?]303) treatment inactivates high levels of Zika virus in red blood cell components", Transfusion [onlime], Feb. 16, 2017 (Feb. 16, 2017) [retrieved on Jun. 27, 2018;], vol. 57, issue 3, part 2, retrieved from the Internet: <DOI: 10.1111/trf. 13993>, pp. 779-789, see entire document, especially, p. 780-786.

* cited by examiner

*Primary Examiner* — Po-Chih Chen
(74) *Attorney, Agent, or Firm* — Dinsmore & Shohl LLP

(57) ABSTRACT

Embodiments of the present invention relate generally the use of compositions comprising a glutathione precursor and a selenium source, e.g., compositions which elevate intracellular glutathione, in the prevention and treatment of Zika viral diseases, e.g., Zika fever. Related embodiments are directed to use of such compositions, e.g., compositions comprising a glutathione precursor and a selenium source, in reducing the infectivity of Zika viruses or Zika viral particles.

20 Claims, 8 Drawing Sheets

COMPOSITIONS AND METHODS FOR THE TREATMENT OF ZIKA VIRAL DISEASES

CROSS-REFERENCE TO RELATED APPLICATIONS

This application is a U.S. National Phase filing of PCT Application No. PCT/PCT/US2018/030500, entitled "COMPOSITIONS AND METHODS FOR THE TREATMENT OF ZIKA VIRAL DISEASES," filed May 1, 2018, which is based upon and claims the benefit of U.S. Patent Application No. 62/500,430, filed on May 2, 2017, the entire contents of which are incorporated herein by reference.

BACKGROUND

Zika virus infection is now an enormous global concern because of its destructive effect on human health and well-being in mosquito-infested regions. See, "Zika virus: a new global threat for 2016," Editorial, Lancet, 9; 387(10014):96, 2016; Al-Qahtani et al., J Infect Dev Ctries, 10(3): 201-7, 2016. During 2016, at least 3 global regions were recognized as outbreak areas by the World Health Organization (WHO). See, Alera et al., Emerg Infect Dis, 21(4): 722-4, 2015; Adams et al., MMWR Morb Mortal Wkly Rep, 65(30): 774-9, 2016; Besnard et al., Euro Surveill, 19(13), 20751, 2014; Borchardt et al., JAAPA, 29(4): 48-50, 2016; Brasil et al., PLoS Negl Trop Dis, 10(4): p. e0004636, 2016. The economic impact of this arthropod-borne infection has been equally enormous, particularly as a result of its devastating effects on the fetus during pregnancy, and the demonstration that the virus persists in semen and genitalia facilitating spread to people even in the absence of infected mosquitos. See, Brasil et al., N Engl J Med, 375(24): p. 2321-2334, 2016; Brasil et al., Lancet, 387(10026): p. 1482, 2016; Brooks et al., MMWR Morb Mortal Wkly Rep, 65(34): p. 915-6, 2016; Broutet et al., N Engl J Med, 374(16): p. 1506-9, 2016; Davidson et al., MMWR Morb Mortal Wkly Rep, 65(28): 716-7, 2016; Deckard et al., MMWR Morb Mortal Wkly Rep, 65(14): 372-4, 2016; Furtado et al., N Engl J Med, 375(4): 394-6, 2016; Rowland et al., J Assist Reprod Genet, 33(4): p. 435-7, 2016; and Musso et al., Emerg Infect Dis, 21(2): p. 359-61, 2015. Given the time required for the testing of newly developed vaccine strategies and the discovery of effective antivirals, it is imperative that scientists also focus on alternate approaches that can negatively impact virus infection.

One approach to enhance discovery of antivirals is to explore the role(s) of the innate immune defenses engaged during Zika virus infection. One of the primordial innate defense responses, conserved across nearly every species, is that of the glutathione (reduced form: GSH; oxidized form: GSSG), which comprises part of the essential antioxidant defense system. Glutathione is also the smallest sulfur-containing protein in the cell and serves to reduce reactive oxygen species generated in cells under oxidative stress. It is also involved in the chelation of divalent metal ions.

Although there is some report that glutathione may impact viruses (see, Fraternale et al., Mol Aspects Med, 30(1-2): 99-110, 2009; Fraternale et al., Curr Med Chem, 13(15): 1749-55, 2006; and Fraternale et al., Antiviral Res, 77(2): p. 120-7, 2008), most of these initial reports involve utilization of whole glutathione, often in reduced form (GSH). These in vitro studies have limited applicability in the context of treating or preventing Zika viral diseases because whole glutathione is poorly transported into cells and therefore provides limited bioavailability.

Oral administration of glutathione to treat various conditions is also largely deemed ineffective and that prodrugs or precursor therapy would be necessary (see, e.g., National Clinical Trials #NCT01251315). Cysteine, or a more bio-available precursor of cysteine, N-acetyl cysteine (NAC), has been suggested as candidates for precursor therapy. While cysteine and NAC are both, themselves, antioxidants, their presence competes with glutathione for resources in certain reducing (GSH recycling) pathways. Since glutathione is a specific substrate for many redox pathways, the loading of a host with cysteine or NAC may result in less efficient utilization or recycling of glutathione. Thus, cysteine and NAC are not ideal GSH prodrugs. Thus, while GSH may be degraded, and non-physiologically transported as amino acids, there is a physiological barrier to the importation of intact glutathione. As such, these conventional methods fail to provide a reliable and safe means for increasing intracellular GSH levels, especially in the therapeutic context.

Additionally, since glutathione has been shown to increase the vestigiality of the glutathione synthetic machinery via negative feedback inhibition of certain enzymes that are critical to its synthesis (see, e.g., Richman et al., J Biol Chem, 250(4):1422-6, 1975), therapy with whole glutathione may pose unintended side effects.

Accordingly, there is an unmet need for new methods for treating or preventing Zika viral diseases such as Zika fever.

SUMMARY OF THE INVENTION

This disclosure relates to method of treating or inhibiting Zika virus infection and Zika viral diseases, by administering to a subject in need thereof an effective amount of a composition that can increase the concentration of intracellular glutathione, such as a composition comprising free form amino acid precursors (FFAAP) of glutathione. Practice of the method can inhibit intracellular replication of Zika virus or infectivity of Zika virus or inhibit both intracellular replication and infectivity of Zika virus.

Embodiments described herein further relate to advantageously treating Zika viral diseases such as Zika fever. For instance, the instant compositions and methods may help eliminate or reduce the Zika viral load and/or titers in affected subjects, cells and/or tissues.

The compositions and methods described herein further provide for the treatment of Zika viral diseases in subjects who need such treatment, e.g., humans and monkeys. Preferably, the compositions and methods described herein are useful for treating a subject diagnosed with Zika virus infection or Zika fever.

In one embodiment, disclosed herein is a method for treating Zika viral disease in a subject in need thereof, comprising administering to the subject, an effective amount of a composition that elevates intracellular glutathione.

In one embodiment, disclosed herein is a method for treating Zika viral disease in a subject in need thereof, comprising administering to the subject, an effective amount of a composition comprising Immune Formulation, i.e., a composition comprising a glutathione precursor and a selenium compound, as disclosed in U.S. Reissue Pat. Nos. 39,734 and 42,645.

In one embodiment, the Zika virus is a virus having the National Center for Biotechnology Information (NCBI) Taxonomy ID No.: 64320.

In another embodiment, disclosed herein is a method for treating Zika viral disease in a subject in need thereof, comprising administering to the subject, a composition comprising the Immune Formulation, i.e., a glutathione precursor and a selenium compound, wherein the composition is administered at an amount effective to reduce the infectivity of the virus.

In another embodiment, disclosed herein is a method for treating Zika viral disease in a subject in need thereof, comprising administering to the subject, a composition comprising the Immune Formulation, i.e., a glutathione precursor and a selenium compound, at an amount effective to reduce the infectivity of the virus by at least 40%. Particularly under this embodiment, the infectivity of the virus is reduced by at least 60%. Especially under this embodiment, the infectivity of the virus is reduced by at least 90%.

In another embodiment, disclosed herein is a method for treating Zika viral disease in a subject in need thereof, comprising administering to the subject, a composition comprising the Immune Formulation, i.e., a glutathione precursor and a selenium compound, at an amount effective to reduce the viral load by at least 40%. Particularly under this embodiment, the viral load is reduced by at least 60%. Especially under this embodiment, the viral load is reduced by at least 90%.

In another embodiment, disclosed herein is a method for treating Zika viral disease in a subject in need thereof, comprising administering to the subject, an effective amount of a composition comprising Immune Formulation, wherein the composition elevates intracellular glutathione and further reduces intracellular replication of the Zika virus. Particularly under this embodiment, the intracellular replication of the Zika virus is reduced by at least 25%. Especially under this embodiment, the intracellular replication of the Zika virus is reduced by at least 50%. Particularly under this embodiment, the intracellular replication of the Zika virus is reduced by at least 80%.

In another embodiment, disclosed herein is a method for treating Zika fever in a subject in need thereof, comprising administering to the subject, an effective amount of a composition comprising Immune Formulation that elevates intracellular glutathione.

In another embodiment, disclosed herein is a method for treating Zika viral disease in a subject in need thereof, comprising administering to the subject, an effective amount of a composition comprising Immune Formulation, wherein the composition comprises glycine, L-cystine, a glutamate source selected from the group consisting of glutamine and glutamic acid and a selenium source.

In another embodiment, disclosed herein is a method for treating Zika viral disease in a subject in need thereof, comprising administering to the subject, an effective amount of a composition comprising Immune Formulation, wherein the composition comprises glycine, L-cystine, a glutamate source selected from the group consisting of glutamine and glutamic acid and a selenium source selected from the group consisting of selenomethionine, selenite, methylselenocysteine and selenium nanoparticles.

In another embodiment, disclosed herein is a method for treating Zika viral disease in a subject in need thereof, comprising administering to the subject, an effective amount of a composition comprising Immune Formulation, wherein the composition elevates intracellular glutathione by at least about 40%.

In another embodiment, disclosed herein is a method for treating Zika viral disease in a subject in need thereof, comprising administering to the subject, an effective amount of a composition comprising Immune Formulation, wherein the composition elevates intracellular glutathione by at least about 25%. Particularly under this embodiment, the composition elevates intracellular glutathione by at least about 30%.

In another embodiment, disclosed herein is a method for treating Zika viral disease in a subject in need thereof, comprising administering to the subject, a composition comprising Immune Formulation, at a dose effective to attain an intracellular concentration of glutathione between 10 µM to 50 µM at 24 hours post-administration.

In another embodiment, disclosed herein is a method for treating Zika viral disease in a subject in need thereof, comprising administering to the subject, a composition comprising Immune Formulation, at a dose effective to attain an intracellular concentration of glutathione between 20 µM to 40 µM at 48 hours post-administration.

In another embodiment, disclosed herein is a method for treating Zika viral disease in a subject in need thereof, comprising administering to the subject, a composition comprising Immune Formulation at a dose that is effective to reduce or inhibit depletion of intracellular glutathione levels in Zika virus-infected cells at 24-48 hours post-administration of the composition.

In another embodiment, disclosed herein is a method for treating Zika viral disease in a subject in need thereof, comprising administering to the subject, a composition comprising Immune Formulation at a dose that is effective to normalize intracellular glutathione levels in Zika virus-infected cells to the intracellular glutathione levels in non-infected cells at 24-48 hours post-administration of the composition.

In another embodiment, disclosed herein is a method for treating Zika viral disease in a subject in need thereof, comprising administering to the subject, a composition comprising Immune Formulation, wherein the composition is administered before or after infection with the virus.

In another embodiment, disclosed herein is a method for treating Zika viral disease in a subject in need thereof, comprising administering to the subject, a composition comprising Immune Formulation, wherein the composition is administered after infection with the virus.

In another embodiment, disclosed herein is a method for treating Zika viral disease in a subject in need thereof, comprising administering to the subject, a composition comprising Immune Formulation, wherein the composition is administered about 12 hours to about 96 hours post-infection with the virus.

In another embodiment, disclosed herein is a method for treating Zika viral disease in a subject in need thereof, comprising administering to the subject, a composition comprising Immune Formulation, wherein the composition is administered about one hour post-infection with the virus.

In another embodiment, disclosed herein is a method for reducing Zika viral load in a biological sample comprising cells, comprising contacting the biological sample with an effective amount of a composition that increases intracellular glutathione.

In another embodiment, disclosed herein is a method for reducing Zika viral load in a biological sample comprising blood cells, neural cells or epithelial cells, comprising contacting the biological sample with an effective amount of a composition that increases intracellular glutathione.

In some embodiments, disclosed herein is a method for treating Zika viral disease in a subject, or reducing the infectivity of a Zika virus in a subject, or reducing Zika viral load in a subject, comprising administering, to the subject, a Zika virus replication inhibiting amount of a composition that increases intracellular glutathione, e.g., a composition comprising glycine; L-cystine; a glutamate source selected from the group consisting of glutamine and glutamic acid; and a selenium source.

In some embodiments, the disclosure relates to a composition comprising glycine; L-cystine; a glutamate source selected from the group consisting of glutamine and glutamic acid; and a selenium source, for use in treating Zika viral disease in a subject, or reducing the infectivity of a Zika virus in a subject, or reducing Zika viral load in a subject.

In some embodiments, the disclosure relates to use of a composition comprising glycine; L-cystine; a glutamate source selected from the group consisting of glutamine and glutamic acid; and a selenium source, for the manufacture of a medicament for treating Zika viral disease in a subject, or reducing the infectivity of a Zika virus in a subject, or reducing Zika viral load in a subject.

In another embodiment, disclosed herein is a use of Immune Formulation, i.e., a composition comprising a glutathione precursor and a selenium compound, as disclosed in U.S. Reissue Pat. Nos. 39,734 and 42,645, in increasing intracellular glutathione levels for therapy of Zika viral diseases, e.g., Zika fever.

In another embodiment, disclosed herein is use of Immune Formulation, i.e., a composition comprising a glutathione precursor and a selenium compound, as disclosed in U.S. Reissue Pat. Nos. 39,734 and 42,645, for the manufacture of a medicament for treating Zika viral disease, e.g., Zika fever.

BRIEF DESCRIPTION OF THE DRAWINGS

The details of one or more embodiments of the invention are set forth in the accompanying drawings/tables and the description below. Other features, objects, and advantages of the invention will be apparent from the drawings/tables and detailed description, and from the claims.

FIG. 4A shows total GSH concentration and FIG. 4B shows viral titers in control (0 mM FFAAP) and treated cells. All experiments shown were performed in triplicates and the data shown are representative data from multiple independent experiments. Standard error bars were calculated using Microsoft Excel and significance assessments were performed using GRAPHPAD PRISM. * indicates a p-value <0.05 and >0.01;  indicates a p-value <0.01 and >0.001; and * indicates a p-value <0.001.

FIG. 5A shows intracellular glutathione levels in Zika virus infected Vero cells that were treated with or without FFAAP (3 mM), and with or without co-treatment with buthionine sulphoximine (BSO), a glutathione depleting agent (200 μM). FIG. 5B shows glutathione levels in Vero cells pre-treated with BSO (200 μM), which were then infected with Zika virus and treated with or without FFAAP. FIG. 5C shows percent Zika virus titer reduction in Vero cells treated with BSO, FFAAP, or BSO+ FFAAP. FIG. 5D shows percent reduction in Zika virus titers in Vero cells pretreated with BSO and then treated with BSO, FFAAP, or BSO+ FFAAP post-infection. All experiments were performed in triplicates and the data shown are representative data from multiple independent experiments. Standard error bars were calculated using Microsoft Excel and significance assessments were performed using GRAPHPAD PRISM. * indicates a p-value <0.05 and >0.01;  indicates a p-value <0.01 and >0.001; and * indicates a p-value <0.001.

FIG. 6A shows intracellular glutathione levels in Zika virus infected JEG-3 cells that were treated with or without FFAAP (3 mM), and with or without co-treatment with buthionine sulphoximine (BSO), a glutathione depleting agent (200 μM). FIG. 6B shows glutathione levels in JEG-3 cells pre-treated with BSO (200 μM), which were then infected with Zika virus and treated with or without FFAAP. FIG. 6C shows percent Zika virus titer reduction in JEG-3 cells treated with BSO, FFAAP, or BSO+FFAAP. FIG. 6D shows percent reduction in Zika virus titers in JEG-3 cells pretreated with BSO and then treated with BSO, FFAAP, or BSO+ FFAAP post-infection. All experiments were performed in triplicates and the data shown are representative data from multiple independent experiments. Standard error bars were calculated using Microsoft Excel and significance assessments were performed using GRAPHPAD PRISM. * indicates a p-value <0.05 and >0.01;  indicates a p-value <0.01 and >0.001; and * indicates a p-value <0.001.

FIGS. 7A-7C show intracellular GSH concentration in African green monkey (*Chlorocebus* sp.) Vero cells. FIG. 7A shows GSH levels at day 0 in uninfected Vero cells; FIG. 7B shows GSH levels at day 2 in uninfected Vero cells; and FIG. 7C shows GSH levels in uninfected Vero cells pretreated with BSO at day 2. FIGS. 7D-7F show intracellular GSH concentration in human placenta JEG-3 cells. FIG. 7D shows GSH levels at day 0 in uninfected JEG-3 cells; FIG. 7E shows GSH levels at day 2 in uninfected JEG-3 cells; and FIG. 7F shows GSH levels in uninfected JEG-3 cells pretreated with BSO at day 2.

DETAILED DESCRIPTION

Figure 1:
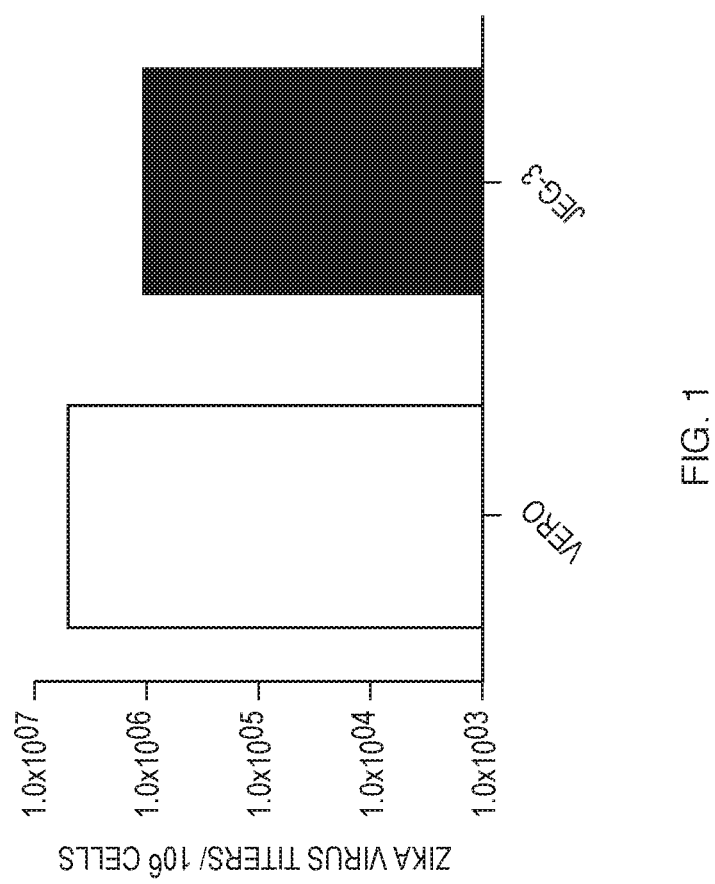
FIG. 1 shows Zika virus production in human placenta choriocarcinoma (JEG-3) cells and non-human primate (African green monkey (*Chlorocebus* sp.)) Vero cells. Cells from each species were grown to mid-log phase and infected with Zika virus (MOI 0.1), which was adsorbed to the monolayers of cells (triplicate wells) for two hours at 37° C. in a humidified environment of 5% $CO_2$: 95% air. Subsequently, growth medium was added and infection continued for 3 days. Infected cells were harvested on day 3 to quantify virus replication. Plaque assays were performed subsequently to quantify the amount of virus produced in each cell line.

Various aspects now will be described more fully hereinafter. Such aspects may, however, be embodied in many different forms and should not be construed as limited to the embodiments set forth herein; rather, these embodiments are provided so that this disclosure will be thorough and complete.

Where a range of values is provided in this disclosure, it is intended that each intervening value between the upper and lower limit of that range and any other stated or intervening value in that stated range is encompassed within the disclosure. For example, if a range of 1 µM to 8 µM is stated, it is intended that 2 µM, 3 µM, 4 µM, 5 µM, 6 µM, and 7 µM are also explicitly disclosed, as well as the range of values greater than or equal to 1 µM and the range of values less than or equal to 8 µM.

The singular forms "a," "an," and "the" include plural referents unless the context clearly dictates otherwise. Thus, for example, reference to an "amino acid" includes a single amino acid as well as two or more of the same or different amino acids; reference to an "excipient" includes a single excipient as well as two or more of the same or different excipients, and the like.

The word "about" means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

As used herein, the term "Immune Formulation," refers to a composition comprising a glutathione precursor and typically also contains a selenium compound, as disclosed in U.S. Reissue Pat. Nos. 39,734 and 42,645 (each of which is incorporated herein in their entirety). Immune Formulation typically comprises a glutamate source (e.g., glutamic acid or glutamine), cystine and glycine. Immune Formulation may further comprise a selenium source which comprises inorganic selenium compound, e.g., aliphatic metal salts containing selenium in the form of selenite or selenate anions or an organic selenium compound, e.g., selenium cystine, selenium methionine, mono- or di-seleno carboxylic acids comprising about seven to eleven carbon atoms in the chain, or a seleno amino acid chelate. The composition makes available two rate-limiting L-cysteines from the disulfide bond of L-cystine. L-cysteine is rate limiting for biosynthesis of glutathione. When the formulation comprises selenomethionine, the composition further makes available an additional rate-limiting L-cysteine via transsulfuration of the methionine moiety in selenomethionine. Accordingly, Immune Formulation provides the full range of the amino acid precursors needed to form the molecule of glutathione. Physiologically synthesized glutathione maximizes immunological pleiotropy and mechanisms of action without risks of reductive stress.

In one embodiment, Immune Formulation provides the selenium co-factor needed to activate glutathione following its synthesis, and it does not bypass the substrate-specific synthetic enzymes, which provides protection against reductive stress. Additionally, Immune Formulation minimizes risk of vestigiality inherent in importing molecular glutathione, which bypasses the substrate-specific enzymes and the quantitative glutathione regulatory feedback mechanism. The precursor method offers bioavailability advantages by providing individual free form amino acids. Immune Formulation is absorbed immediately into the buccal mucosa. The disulfide bond utilizes the recycling and coupling properties for maintaining and replenishing the rate-limiting L-Cysteine. The free form amino acids provided with Immune Formulation are resistant to degradation and high temperatures; and protected from vigorous agitation and wide pH variation, as compared to high molecular weight whey protein.

The term "restore," as used herein, refers to a return to an original state or normal state of intracellular glutathione levels after depletion or loss following Zika virus infection.

A "subject" or "patient" can be any animal, particularly a mammal, and including, but by no means limited to, humans, domestic animals, such as feline or canine subjects, farm animals, such as but not limited to bovine, equine, caprine, ovine, avian and porcine subjects, wild animals (whether in the wild or in a zoological garden), research or laboratory animals, such as mice, rats, rabbits, goats, sheep, pigs, dogs, cats, etc., avian species, such as chickens, turkeys, songbirds, and the like.

As used herein, the terms "treating" refers to the use or administration of a composition, as described herein, including "Immune Formulation," to treat or prevent a pathologic condition, such as Zika virus infection and Zika viral disease. Accordingly, treatment can be curative, palliative (e.g., control or mitigate a disease or disease symptoms) or prophylactic (e.g., reduce the frequency of, or delay the onset of a pathologic condition (e.g., Zika fever) or symptoms in a subject relative to a subject not receiving treatment). This can include reversing, reducing, or arresting the symptoms, clinical signs, and underlying pathology of a condition in a manner to improve or stabilize a subject's condition (e.g., regression of fever).

In order to provide a complete, concise and clear description of the invention, this disclosure includes descriptions of various components, groups of components, ranges and other elements of the broad invention. It is intended that such elements can be variously combined to provide embodiments of the invention. It is also intended that any disclosed features (e.g., substituent, analog, compound, ligand, structure, component) including individual members of any disclosed group, including any sub-ranges or combinations of sub-ranges within the group, may be excluded from the invention or any embodiments of the invention for any reason.

Overview

This disclosure relates to methods for treating and/or preventing Zika viral diseases, e.g., Zika fever, Zika virus infection. In general, the methods include administering an effective amount of a compound or composition that increases the levels of intracellular glutathione to a subject in need thereof, such as a subject infected by Zika virus or at risk of Zika virus infection (e.g., a person living in a geographic area in which Zika virus is endemic, or in which there is an outbreak). For example, compositions containing glutathione precursors can be administered to inhibit Zika virus infectivity and/or Zika virus replication.

As described and exemplified herein, the inventors discovered that treatment of cells with a composition containing free-form amino acid precursors of glutathione (FFAAP) increased intracellular glutathione levels in the cells. Surprisingly, FFAAP concomitantly inhibited the replication of Zika virus by up to 90% in treated cells in a dose-dependent manner. Additionally, FFAAP also significantly reduced the ability of Zika viruses to form plaques, thus demonstrating the ability of FFAAP to inhibit Zika viral infectivity. The protective effect against Zika virus was observed as early as 24 hours post infection and sustained beyond 72 hours post-infection. Further studies described and exemplified herein demonstrated that total cellular glutathione levels are dramatically decreased in cells infected with Zika virus, but that this decrease in glutathione levels was reduced by FFAAP treatment, as was Zika virus replication. These results establish the surprising inhibitory effect of FFAAP against Zika virus replication and infectivity. Additionally, the results establish that FFAAP treatment relieves the stress inflicted by Zika virus infection and replication and exerts a protective effect on treated cells. Without wishing to be bound by any particular theory, it is believed that the Zika-inhibiting effects of FFAAP are due to the direct or indirect actions of elevated glutathione levels induced by FFAAP. Accordingly, methods for the treatment of Zika viral diseases, e.g., Zika fever, and compositions suitable for use in the methods are disclosed herein Compositions and Methods This disclosure provides a method for treating Zika viral disease, comprising administering to a subject in need thereof, an effective amount of a composition that increases the levels of intracellular glutathione.

A. Compositions

Compositions suitable for use in the methods disclosed herein can be administered to a subject to increase the level of intracellular glutathione in the subject. Exemplary compositions can contain, for example, reduced glutathione, oxidized glutathione and/or conjugated glutathione, preferably formulated with a suitable delivery system (e.g., liposomes, nanoparticles and the like) to provide for intracellular delivers of the glutathione. Preferred compositions for use in the methods disclosed herein contain FFAAP. More preferred compositions for use in the methods disclosed herein contain FFAAP and a selenium source. Particularly preferred compositions are Immune Formulations.

The Immune Formulation used in the methods described herein typically comprises (a) glycine; (b) L-cystine; and (c) a L-glutamate source (e.g., L-glutamine or L-glutamate), each as a free-form amino acid. The Immune Formulation typically further comprises (d) a selenium source, such as a selenium-containing amino acid (e.g., selenium methionine, selenium cysteine, methylselenocysteine), selenite, or selenium nanoparticles. While each of the a) glycine, (b) L-cystine, (c) glutamate source, and (d) a selenium source are typically components of a single composition, they can be administered in the form of two or more separate compositions if desired.

If desired, the Immune Formulation can comprise a derivative of one or more of a) glycine, (b) L-cystine, (c) L-glutamate source, and (d) a selenium source. The "derivative" as used herein includes salts, amides, esters, enol ethers, enol esters, acetals, ketals, acids, bases, solvates, hydrates or prodrugs of the free-form amino acids. Such derivatives may be readily prepared by those of skill in this art using known methods for such derivatization. The derivatives suitable for use in the methods described herein may be administered to animals or humans without substantial toxic effects and either are biologically active or are prodrugs.

In one example, the derivatives comprise salts of the amino acids. The term "salt" includes salts derived from any suitable of organic and inorganic counter ions well known in the art and include, by way of example, hydrochloric acid salt or a hydrobromic acid salt or an alkaline or an acidic salt of the aforementioned amino acids.

If desired, the derivative can in addition or alternatively, be solvent addition forms, e.g., a solvate or alcoholate. Solvates contain either stoichiometric or non-stoichiometric amounts of a solvent, and may be formed during the process of crystallization with acceptable solvents such as water, ethanol, and the like. Hydrates are formed when the solvent is water; alcoholates are formed when the solvent is alcohol. Solvates of compounds described herein can be conveniently prepared or formed using routine techniques. The derivative can further comprise amides or esters of the amino acids and/or isomers (e.g., tautomers or stereoisomers) of the amino acids, as desired.

Typically the Immune Formulation is a mixture of a) glycine, (b) L-cystine, (c) glutamate source, and (d) a selenium source. The term "mixture" refers to a mingling together of two or more substances without the occurrence of a reaction by which they would lose their individual properties. The mixture may contain (a) glycine, (b) L-cystine, (c) glutamate source, and (d) a selenium source in suitable amounts or ratios. For example, the mixture can contain a stoichiometreic ratio of L-glutamate:L-cystine:glycine (mole:mole:mole) of e.g., between 4:1:4 to 1:4:1, including, a ratio of 3:1:4, a ratio of 2:1:4, a ratio of 1:1:4, a ratio of 4:1:3, a ratio of 4:1:2, a ratio of 4:1:1, a ratio of 2:1:3, a ratio of 2:1:2, a ratio of 2:1:1, a ratio of 1:1:2, a ratio of 1:2:1, a ratio of 2:2:1, a ratio of 1:2:2, a ratio of 1:3:1, etc. A preferred mixture comprises a stoichiometric ratio of L-glutamate:L-cystine:glycine of about 1:0.5:1 (mole:mole:mole).

Preferably, the Immune Formulation further comprises a selenium source, e.g., selenomethionine, methylselenocysteine, selenite, or selenium nanoparticles. In such compositions the selenium source is present in an amount sufficient to provide a dose of at least about 0.01 mcg to about 20 mcg of selenium. For example, the selenium source is present in an amount sufficient to provide a dose of at least about 0.02 mcg, about 0.03 mcg, about 0.04 mcg, about 0.05 mcg, about 0.06 mcg, about 0.07 mcg, about 0.08 mcg, about 0.09 mcg, about 0.1 mcg, about 0.2 mcg, about 0.3 mcg, about 0.4 mcg, about 0.5 mcg, about 0.6 mcg, about 0.7 mcg, about 0.8 mcg, about 0.9 mcg, about 1 mcg, about 1.1 mcg, about 1.2 mcg, about 1.3 mcg, about 1.4 mcg, about 1.5 mcg, about 1.6 mcg, about 1.7 mcg, about 1.8 mcg, about 1.9 mcg, about 2.0 mcg, about 2.1 mcg, about 2.2 mcg, about 2.3 mcg, about 2.4 mcg, about 2.5 mcg, about 2.6 mcg, about 2.7 mcg, about 2.8 mcg, about 2.9 mcg, about 3.0 mcg, about 3.1 mcg, about 3.2 mcg, about 3.3 mcg, about 3.4 mcg, about 3.5 mcg, about 3.6 mcg, about 3.7 mcg, about 3.8 mcg, about 3.9 mcg, about 4.0 mcg, about 4.1 mcg, about 4.2 mcg, about 4.3 mcg, about 4.4 mcg, about 4.5 mcg, about 4.6 mcg, about 4.7 mcg, about 4.8 mcg, about 4.9 mcg, about 5.0 mcg, about 5.5 mcg, about 6.0 mcg, about 7 mcg, about 8 mcg, about 9 mcg, about 10 mcg, about 11 mcg, about 12 mcg, about 13 mcg, about 14 mcg, about 15 mcg, about 16 mcg, about 17 mcg, about 18 mcg, about 19 mcg, about 20 mcg or more.

The mixtures of a) glycine, (b) L-cystine, and (c) glutamate source, and optionally (d) a selenium source can be made using any suitable methods. For example, when the composition is in the form of a flowable solid (e.g., granulated, dry powder and the like) the individual components can be micronized, milled or otherwise processed to achieve a desired particle size before or after mixing.

The compositions used in the methods described herein may comprise a suitable carrier. As used herein, the term "carrier" includes emulsions, suspensions, gels, sols, colloids, and solids that are physiologically and/or pharmaceutically acceptable. Suitable carries are well-known in the art and include, but are not limited to, aqueous solvents, alcohols, particularly polyhydroxy alcohols such as propylene glycol, polyethylene glycol, glycerol, and vegetable and mineral oils. The carriers and/or excipients can be added in various concentrations and combinations to form solutions, suspensions, oil-in-water emulsions or water-in-oil emulsions. If desired, the carrier may be buffered, for example with alkaline buffers, e.g., ammonium buffer, acidic buffers, e.g., ethanoates, citrates, lactates, acetates, etc., or zwitterionic buffers, such as, glycine, alanine, valine, leucine, isoleucine and phenylalanine, Kreb's-Ringer buffer, TRIS, MES, ADA, ACES, PIPES, MOPSO, cholamine chloride, MOPS, BES, TES, HEPES, DIPSO, MOBS, TAPSO, acetamidoglycine, TEA, POPSO, HEPPSO, EPS, HEPPS, Tricine, TRIZMA, Glycinamide, Glycyl-glycine, HEPBS, Bicine, TAPS, AMPB, CHES, AMP, AMPSO, CAPSO, CAPS, and CABS.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. If desired tonicity adjusting agents can be included, such as, for example, sugars, sodium chloride or combinations thereof. In some embodiments, the composition is isotonic.

The compositions may also include additional ingredients, such as acceptable surfactants, co-solvents, emollients, agents to adjust the pH and osmolarity and/or antioxidants to retard oxidation of one or more component.

In one embodiment, the composition (e.g., an Immune Formulation) may be formulated as a solution having a concentration of between about 10 μM to about 500 mM, depending on the method of solubilization. Especially, the free form amino acid precursor (FFAAP) may be formulated at a concentration of about 1 mM to about 50 mM, including any value in between, e.g., about 0.5 mM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 50 mM, about 60 mM, about 70 mM, about 80 mg/m, about 90 mM, about 100 mM, about 150 mM, about 200 mM, about 250 mM, about 300 mM, about 400 mM, or more.

The compositions can be prepared for administration by any suitable route as oral, parenteral, intranasal, anal, vaginal, topical, subcutaneous and intravenous administration. For oral administration, the composition may be formulated as, for example, a solution, suspension, emulsion, tablet, pill, capsule (e.g., hard or soft shelled gelatin capsules), sustained release formulation, buccal composition, troche, elixir, syrup, wafer, powder or combinations thereof. Oral compositions may be incorporated directly with the food of the diet. Preferred carriers for oral administration comprise inert diluents, edible carriers or combinations thereof.

If desired, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing.

Additional formulations which are suitable for other modes of administration include suppositories. Moreover, sterile injectable solutions may be prepared using an appropriate solvent. Generally, dispersions are prepared by incorporating the various sterilized amino acid components into a sterile vehicle which contains the basic dispersion medium and/or the other ingredients. Suitable formulation methods for any desired mode of administration are well known in the art (see, generally, Remington's Pharmaceutical Sciences, 18th Ed. Mack Printing Company, 1990).

B. Methods

This disclosure provides a method for treating Zika viral disease, comprising administering to a subject in need thereof, an effective amount of a composition that increases the levels of intracellular glutathione.

In some aspects, the method includes monitoring the subject after the composition that increases the levels of intracellular glutathione is administered, for example to determine efficacy and/or to adjust dosing or dosing interval. Suitable methods to monitor subjects with Zika virus infection or Zika virus disease are known in the art. See, e.g., Sacramento et al., "The clinically approved antiviral drug sofosbuvir inhibits Zika virus replication," *Sci Rep.* 7: 40920, 2017 (PMID: 28098253); Abbink et al., "Protective efficacy of multiple vaccine platforms against Zika virus challenge in rhesus monkeys," *Science,* 353(6304):1129-32, 2016 (PMID 27492477). The efficacy of treatment using the composition is preferably evaluated by examining the subject's symptoms in a quantitative way, e.g., by noting a decrease in the frequency of adverse symptoms, behaviors, or attacks, or an increase in the time for sustained worsening of symptoms. In a successful course of treatment, the subject's status will improved (i.e., frequency of relapses will have decreased, or the time to sustained progression will have increased). The most common symptoms of Zika infection are fever, rashes, headaches, joint pain, conjunctivitis (red eyes), muscle pain, etc. Zika infections are usually mild with symptoms lasting for several days to a week.

In particular applications, the method is for delaying progression, delaying onset, slowing progression, preventing, providing remission, and/or improving symptoms of Zika viral diseases. For example, the method can be for reducing the incidence, duration, or intensity of fever, rashes, headaches, joint pain, conjunctivitis (red eyes), muscle pain, neurological developmental effects, or any combination thereof that are associated with Zika virus infection, comprising administering to a subject in need thereof, an effective amount of a composition that increases the level of intracellular glutathione.

In the practice of any of the methods disclosed herein, the composition increases the level of intracellular glutathione and can be administered to a subject who is infected by Zika virus or who is at risk of infection by Zika virus, such as a person living or traveling in an area where Zika virus is endemic. In certain embodiments of the methods, the subject is infected by Zika virus. In other embodiments of the methods, the subject is at risk of infection by Zika virus. In a particular practice of the methods disclosed herein, the composition that increases the level of intracellular glutathione is administered to the subject at the onset of infection or as soon as practicable after infection, or prior to the expiration of 12-hours post infection (HPI), 24 HPI (1 DPI), 48 HPI (2 DPI), 72 HPI (3 DPI) or 96 HPI (4 DPI).

Preferably, the composition that is administered in any of the methods disclosed herein is an Immune Formulation, such as IMMUNE FORMULATION 200 (mixture of glycine, an L-glutamate source, L-cystine, and L-seleno-methionine, ProImmune Research Institute, Rhinebeck, NY).

The composition that increases the level of intracellular glutathione (e.g., Immune Formulation, IMMUNE FORMULATION 200 (mixture of glycine, an L-glutamate source, L-cystine, and L-seleno-methionine, ProImmune Research Institute, Rhinebeck, NY)) can be administered to the subject in need thereof using any suitable or desired mode of administration. For example, the composition can be administered parenterally (e.g., intravenously, intramuscularly, subcutaneously, intraperitonealy, intradermally, intra-articularly, intrathecally, epidurally, intracerebrally), by buccal administration, rectally, topically, transdermally, orally, intranasally, by pulmonary route, intra-opthalmically and retro-orbitally. Parenteral administration (e.g., intravenous administration) can include bolus injection, intermittent infusion, or continuous infusion. Oral and/or buccal administrations are generally preferred.

An effective amount of the composition that increases the level of intracellular glutathione (e.g., Immune Formulation, IMMUNE FORMULATION 200 (mixture of glycine, an L-glutamate source, L-cystine, and L-seleno-methionine, ProImmune Research Institute, Rhinebeck, NY)) is administered to a subject in need thereof in the practice of the methods of the invention. An "effective amount" is an amount that is sufficient to achieve the desired effect under the conditions of administration, such as an amount that is sufficient to increase the level of intracellular glutathione, to reduce infectivity or replication of Zika virus, to reverse or reduce depletion of intracellular glutathione levels in Zika virus-infected cells, to restore intracellular glutathione levels in Zika virus-infected cells, or to reduces the progress of, cures or acts palliatively on Zika virus infection or Zika viral disease, e.g., Zika fever. The actual amount administered may depend on a variety of factors including the subject's age, general health, body weight, severity of condition, the type of disease being treated, previous or concurrent therapeutic interventions, and other factors. Appropriate amounts to be administered can be determined by a clinician based on these and other considerations. The effective amount can be administered in a single dose or in multiple doses including in a dosing regimen or course of therapy.

When the composition is an Immune Formulation, such as IMMUNE FORMULATION 200 (mixture of glycine, an L-glutamate source, L-cystine, and L-seleno-methionine, ProImmune Research Institute, Rhinebeck, NY)) typically an amount that that provides a combined dose of glycine plus L-glutamate source plus L-cysteine from about 0.25 g to about 10.0 g, such as, about 0.50 g, about 0.75 g, about 1.0 g, about 1.25 g, about 1.50 g, about 1.60 g, about 1.75 g, about 2.0 g, about 2.25 g, about 2.5 g, about 2.75 g, about 3.0 g, about 4.0 g, about 5.0 g, about 6.0 g, about 7.0 g, about 8.0 g, about 9.0 g or about 10.0 g or more is administered to a human patient at each administration. If weight adjusted dosing is desired or indicated, an amount that provides a combined dose of glycine plus L-glutamate source plus L-cysteine of about 1 mg/kg/body weight to about 100 g/kg/body weight or more can be administered, for example, about 2 mg/kg/body weight, about 5 mg/kg/body weight, about 10 mg/kg/body weight, about 15 mg/kg/body weight, about 20 mg/kg/body weight, about 25 mg/kg/body weight, about 30 mg/kg/body weight, about 40 mg/kg/body weight, about 50 mg/kg/body weight, about 100 mg/kg/body weight, or about 200 mg/kg/body weight, or more at each administration.

In some examples of the practice of the methods disclosed herein, the effective amount increases intracellular glutathione levels by at least about 20%, at least about 30%, at least about 40%, at least about 50%, at least about 60%, at least about 70%, at least about 80%, at least about 90%, at least about 100%, at least about 120%, at least about 150%, at least about 200%, at least 300% (e.g., compared to pre-treatment level). The effective amount can be an amount that results in an intracellular glutathione concentration of between about 10 μM to about 100 μM, particularly between about 20 μM and about 60 μM, and especially between about 30 μM and about 50 μM, including, a concentration of glutathione of about 10 μM, about 11 μM, about 12 μM, about 13 μM, about 14 μM, about 15 μM, about 16 μM, about 17 μM, about 18 μM, about 19 μM, about 20 μM, about 21 μM, about 22 μM, about 23 μM, about 24 μM, about 25 μM, about 26 μM, about 27 μM, about 28 μM, about 29 μM, about 30 μM, about 31 μM, about 32 μM, about 33 μM, about 34 μM, about 35 μM, about 36 μM, about 37 μM, about 38 μM, about 39 μM, about 40 μM, about 41 μM, about 42 μM, about 43 μM, about 44 μM, about 45 μM, about 50 μM, about 60 μM, about 70 μM, about 80 μM, about 90 μM, about 100 μM, about 200 μM, about 500 μM, or more. In some embodiments, the effective amount can be an amount that results in an intracellular glutathione concentration of about 1 mM or more, e.g., 1.5 mM, 2.0 mM, 2.5 mM, 3.0 mM, 3.5 mM, 4 mM, 4.5 mM, 5 mM, 6.0 mM, 7.0 mM, 8.0 mM, 9.0 mM, 10 mM, or more. Typically, the increase in intracellular glutathione concentrations is attained about 2 hours to about 72 hours following administration of the composition. Methods of quantitating intracellular glutathione levels, e.g., in terms of concentration or weight ratio (e.g., nano moles/mg of cell protein), are known in the art and exemplified herein. In one embodiment, the concentration values are based on the average calculated volume of the cell type used (e.g., Vero cells having a volume of about ~0.6 pico liter (pL)/cell) and the glutathione concentration/cell is approximated by first quantifying the total moles of glutathione per unit volume (of media) and then arriving at the intracellular concentration by factoring in the cell volume.

In some examples of the practice of the methods disclosed herein, the effective amount of glutathione reduces infectivity of Zika virus by at least about 20%, at least about 30%, at least about 40%, at least about 50%, at least about 60%, at least about 70%, at least about 80%, at least about 90%, at least about 95% or more, compared to controls (e.g., an untreated sample or a sample treated with a buffer alone).

In some examples of the practice of the methods disclosed herein, the effective amount reduces intracellular replication of Zika virus by at least about 20%, at least about 30%, at least about 40%, at least about 50%, at least about 60%, at least about 70%, at least about 80%, at least about 90%, at least about 95% or more, compared to controls (e.g., an untreated sample or a sample treated with a buffer alone).

In some examples of the practice of the methods disclosed herein, the effective amount is sufficient to restore intracellular glutathione levels in Zika virus-infected cells. Typically, the total intracellular glutathione level, e.g., combined levels of oxidized and reduced glutathione, is restored.

In some examples of the practice of the methods disclosed herein, the effective amount is sufficient to reverse or reduce depletion of intracellular glutathione levels in Zika virus-infected cells. As demonstrated in the Examples section, Zika virus elicits oxidative stress, resulting in depletion of intracellular glutathione. Treatment of Zika-infected cells with the compositions can reverse or reduce the oxidative stress. In some embodiments, a reversal or reduction in Zika-virus-elicited depletion of intracellular glutathione is achieved 4-48 hours post-administration.

In some examples of the practice of the methods disclosed herein, the effective amount is sufficient to produce intracellular concentration of the active components of the composition (e.g., the FFAAP, such as the combined amounts of L-glutamate, L-cystine and glycine) of at least about 2 mM, about 2 mM to about 5 mM, or about 2.5 mM to about 5 mM.

In a further aspect, the disclosure relates to a method for killing or inhibiting the replication of Zika virus in a biological sample, comprising contacting the biological sample with an effective amount of a composition that increases the level of intracellular glutathione (e.g., Immune Formulation, IMMUNE FORMULATION 200 (mixture of glycine, an L-glutamate source, L-cystine, and L-selenomethionine, ProImmune Research Institute, Rhinebeck, NY)). As used herein, a "sample" refers to any biological sample that contains Zika virus infected cells or Zika virus (including, but not limited to, conditioned medium resulting from the growth of cells in cell culture medium, Zika virus infected cells, and the like).

In another embodiment, disclosed herein is a method for reducing Zika viral load in a biological sample comprising cells, comprising contacting the biological sample with an effective amount of a composition that increases intracellular glutathione.

In another embodiment, disclosed herein is a method for reducing Zika viral load in a biological sample comprising blood cells, neural cells or epithelial cells, comprising contacting the biological sample with an effective amount of a composition that increases intracellular glutathione.

Combination Therapies

If desired, the methods disclosed herein can further include administering one or more additional therapeutic agents to the subject in need thereof, such as an agent that is effective in the treatment of Zika viral diseases or conditions. Examples of agents that can be used in the methods described herein include antivirals, such as niclosamide, sofosbuvir, PHA-690509, emricasan or a phytochemical having anti-viral effects. See, Byler et al. *J Mol Graph Model*, 69:78-91, 2016. The additional therapeutic agent and the composition that increases intracellular glutathione levels are administered so as to provide substantial overlap in their biological activities, and can be administered as components of a single composition or as separate compositions. An effective amount of the additional therapeutic agent is administered and the appropriate amount can be determined based on the subject's age, general health, body weight, severity of condition, the type of disease being treated, previous or concurrent therapeutic interventions, and other factors.

EXAMPLES

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

Example 1

Cells and virus

Each cell line was procured through ATCC®. Vero cells (ATCC®—CCL81) were grown in Eagles minimal essential medium (MEM) supplemented with 10% fetal bovine serum (FBS) as recommended by ATCC®. Cells used were passaged no more than 20 times before use, with cells received from ATCC® between passage 127-130. Human placental cells JEG-3 (ATCC® HTB-36™) (Manassas, VA), were grown in Eagle's Minimum Essential Medium (ATCC, Catalog No. 30-2003) with 10% fetal calf serum (FCS). Virus infections were initiated on monolayers of semi-confluent cells in log phase growth by removing medium, adding minimum volume virus stock to achieve the specific multiplicity of infection used for adsorption during a 90-min incubation. Virus, which remained, was removed following adsorption, and growth medium, i.e., MEM supplemented with 2% FBS in semi-solid medium was added for subsequent quantification of plaques described below.

Cell Quantification and Viability

Cell numbers were quantified using a hemocytometer to accurately count cells manually at 10× magnification. An aliquot of each sample was placed into an equal volume of Trypan Blue and gently mixed; then 10 µL of cells were added to each side of the hemocytometer under the coverslip. Live, treated cells were counted to calculate the percent of viable treated cells versus the percent of live cells in the untreated samples.

FFAAP Treatment of Vero Cells

Uninfected Vero cells were treated with 0, 2, 4, 6 mM concentrations of free-form amino acid precursors (FFAAP) for 72 hours. Vero cells infected with Zika virus were treated with the above concentration immediately for quantification of virus titers. For plaque enumeration assay Vero cells were treated with FFAAP at the time of adsorption and the treatment was continued for 3 days in semi-solid medium. For these assays, the concentration of FFAAP used to treat the cells/virus was 0, 2.5, 5.0, up to 10 mM.

FFAAP treatment of cells. Uninfected Vero and JEG-3 cells were treated initially with 0, 2, 4, 6 mM concentrations of FFAAP for 72 hours for safety studies, and for subsequent infections the highest concentration, which demonstrated no effects on cell propagation and viability, was selected for each cell line in all subsequent experiments. Cells infected with Zika virus were treated with the above concentration 1.5 hours post adsorption for quantification of virus titers. For plaque enumeration assay cells were treated with FFAAP at the time of adsorption and the treatment was continued for 3 days in semi-solid medium. For these assays the final concentrations in the cell culture medium of the infected and uninfected cells were 0, 2.5, 5.0, and 10 mM FFAAP from solubilized stock solution prepared for FFAAP. Inhibitory concentration ($IC_{50}$) was used as per definitions provided by GRAPHPAD Software) to evaluate dose-response curves.

Plaque Enumeration Assay

In the first study exploring the effects of free-form amino acid precursors (FFAAP) on Zika virus, nearly confluent monolayers of treated and untreated cells were infected with approximately 100 plaque-forming units (PFU) (or infectious particles) of Zika virus or mock-infected cell lysate, which adsorbed for 2 hours at 37° C. in a humidified incubator with 5% $CO_2$: 95% air. Inoculum was removed, and cells overlaid with agarose in MEM supplemented with 2% FBS. Cells were then grown for 72 hours in the presence of FFAAP, semi-solid medium removed, wells rinsed, then stained with crystal violet to count individual plaques to quantify replication of Zika virus with and without treatment. Numbers of plaques from treated wells were normalized against the numbers of plaques in untreated cells to establish percent reduction in infected cells.

Quantification of Zika Virus Titers

Approximately 95% sub-confluent Vero cells or JEG-3 cells were infected Zika in a 48-well plate. After 1.5 hours post-adsorption (HPA), virus inoculum was removed and media with or without FFAAP was added to the respective wells. At 24, 48, and 72 HPI (1, 2, or 3 DPI, respectively), supernatants were collected and frozen at −80° C. until plaque assays were done to determine the virus titers.

Glutathione Precursors and Glutathione Assays. The FFAAP was provided by PROIMMUNE Research Institute, and comprises a mixture of free-form glycine, an L-glutamate source, L-cystine, and L-seleno-methionine (IMMUNE FORMULATION 200®, ProImmune Research Institute, Rhinebeck, NY) as previously described. The FFAAP was solubilized and diluted to achieve the levels shown below. Intracellular glutathione levels (GSSG/GSH) were measured to quantify the levels of newly biosynthesized intracellular glutathione with molar quantities calculated using standard curves prepared with reduced and oxidized glutathione (Enzo Life Sciences, Farmingdale, NY), Standard error of the mean (SEM) was calculated using values from triplicate samples and coefficient of variance was calculated within each sample for each specific treatment group. Statistical analysis was performed with MICROSOFT EXCEL and GRAPH PAD PRISM™ software, which were used to calculate p-values and multiple t test comparisons, respectively. Multiple group analysis was also performed using multiple t-test and t-test for two groups at a time. The results were consistent across multiple assay formats. Multiple group analysis was used to determine if the groups differed from each other. Inhibition of the glutathione biosynthesis pathway was accomplished by using the well-documented inhibitor, BSO, or buthionine-(S,R)-sulfoximine (Sigma-Aldrich, St. Louis, MO). Effective blockade was assessed by measurements of intracellular reduced and oxidized glutathione in the presence of inhibitor.

Results

Cell culture models using Vero cells and JEG-3, human placental cells have each been validated by previous studies as a system supporting robust replication of the Zika virus (see, Chan et al., *Emerging Microbes & Infections,* 5:e93, 2016). To ensure that the cells used in the instant study also supported Zika virus replication, cells from each species were grown to mid-log phase and infected with Zika virus (MOI 0.1). To facilitate infection, Zika virus was adsorbed to the monolayers of cells (triplicate wells) for two hours at 37° C. in a humidified environment of 5% $CO_2$: 95% air. Subsequently, growth medium was added and infection continued for three days. Infected cells were harvested on day three to quantify virus replication. Plaque assays were performed subsequently to quantify the amount of virus produced in each cell line. The results, which are shown in FIG. 1, demonstrate that both human (JEG-3) and non-human primate (Vero) cell-lines support Zika virus replication.

Figure 2:
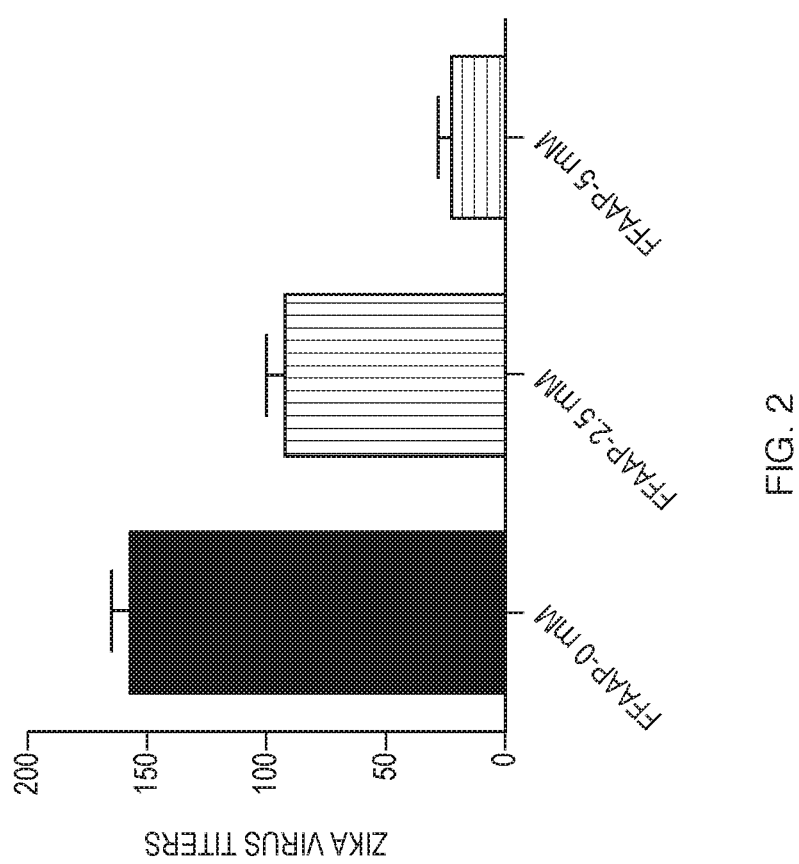
FIG. 2 shows the effect of free-form amino acid precursors of glutathione (FFAAP), e.g., a composition comprising glycine, L-cystine, and an L-glutamate source, together with a selenium source, on Zika virus plaque formation. African green monkey (*Chlorocebus* sp.) Vero cells were adsorbed for 2 h with approximately 100 infectious virions per well (triplicate) of Zika virus (MOI 0.02) and inoculum replaced with MEM containing 2% agarose and supplemented with 2% FBS. Cells were incubated for 3 days, after-which the semi-solid medium was removed, and wells stained with crystal violet. Plaques were enumerated using standard counting methods. Standard error of the means was calculated using MICROSOFT EXCEL or GRAPHPAD PRISM.

In order to determine the anti-viral capability of free-form amino acid precursor of glutathione (FFAAP), Vero cells were infected mid-log phase with Zika virus (strain PRV59) at MOI 0.1. Following a two-hour adsorption of virus at 37° C. in a humidified environment of 5% $CO_2$: 95% air, semi-solid MEM growth medium with different concentrations of FFAAP was added and infection in triplicate samples continued for 3 days. The efficacy of FFAAP on Zika virus infection was measured by counting plaques and $IC_{50}$ was determined. The results, which are shown in FIG. 2, demonstrate that FFAAP treatment significantly reduces Zika virus titers. In particular, the results show that treatment with 2.5 mM FFAAP resulted in about 40% reduction in viral titers compared to untreated controls, while treatment with 5 mM FFAAP resulted in about 80% reduction in viral titers compared to untreated controls.

Figure 3:
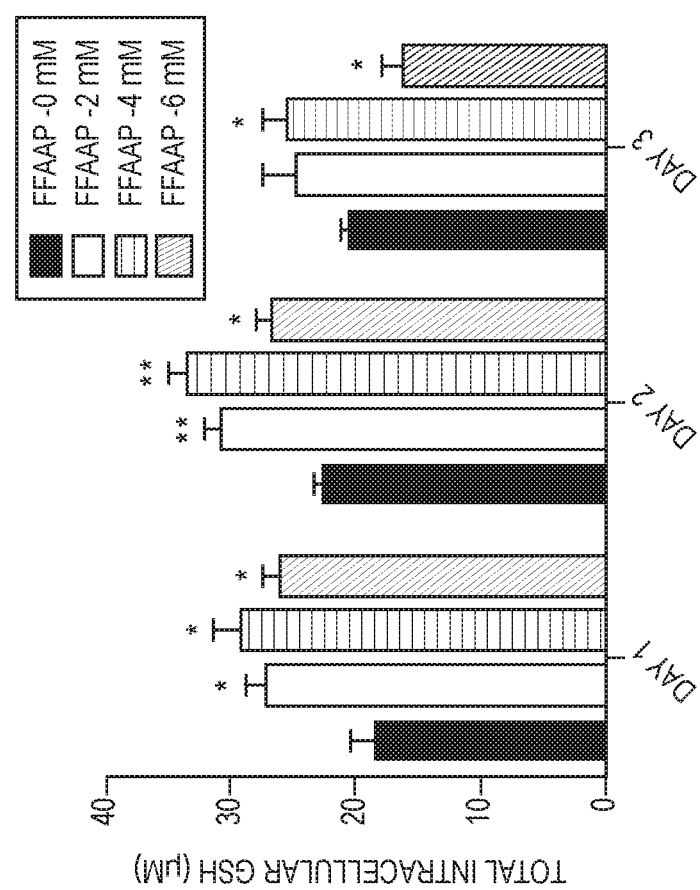
FIG. 3 shows the effects of FFAAP on levels of total intracellular glutathione in healthy cells. African green monkey (*Chlorocebus* sp.) Vero cells, grown to approximately 90-95% confluence (mid-log phase), were treated with and grown in the presence of increasing concentrations of FFAAP for three days. At each time point, medium was discarded and cells were harvested to measure intracellular concentrations of total GSH. All experiments shown were done in triplicate and the data shown are representative data from multiple independent experiments performed. Standard error bars were calculated using MICROSOFT EXCEL and significance assessments were performed using GRAPHPAD PRISM. * indicates a p-value <0.05 and >0.01;  indicates a p-value <0.01 and >0.001; and * indicates a p-value <0.001.

To determine the levels of intracellular glutathione in uninfected cells, FFAAP-treated and untreated cells, we quantified GSH/GSSG levels in each cell line over three days. Growth and viability of the cells were also assessed. Cells were harvested one, two and three days post-treatment (HPT). No significant differences in growth were noted between FFAAP-treated cells, using concentrations bracketing the $IC_{50}$, and untreated cells. FIG. 3 shows relative levels of total intracellular glutathione (GSH+ GSSG) in triplicate cell wells grown in the presence or absence of treatment. Little-to-no oxidized GSH (GSSG) was detected in uninfected cells. Analysis of these data confirmed that treated cells produced significantly more intracellular glutathione (GSH) than untreated cells, as observed from quantification of reduced glutathione (GSH), commensurate with previously published data. On day two, untreated cells produced 15-20 µM of reduced glutathione, whereas FFAAP-treated cells produced up to 30% more GSH by one day post-treatment (DPT).

Next, trypan blue exclusion and MTT assays were used to assess the health of the treated cells. With increasing concentrations of FFAAP (4-6 mM), biosynthesis of total intracellular GSH increased slightly by two DPT and by three DPT, levels began to approach values comparable to those observed in untreated cells, suggesting that FFAAP was no longer stimulating increased biosynthesis of intracellular glutathione. Another possibility is that between two and three DPT, glutathione was conjugated to cellular or viral molecules for removal, and therefore was not measurable.

Glutathione biosynthesis is one of the principal defenses for protecting the cell against excess oxidative events. Glutathione also conjugates cellular constituents for biotransformation and subsequent removal of toxic cell constituents. In the conjugated form, glutathione is no longer detectable in the assays used here and this may explain the reduction in relative levels of GSH/GSSG at 3 DPT as shown in FIG. 3. Re-addition could stimulate an additional increase. The current data demonstrate that FFAAP increases intracellular biosynthesis of total intracellular glutathione relative to untreated cells in an FFAAP dose-dependent manner, plateauing at 4 mM concentrations. Higher levels had no effect on increasing intracellular biosynthesis. Thus, subsequent studies were performed in the presence of $IC_{50}$ levels of FFAAP, as determined for each cell line.

Figure 4B:
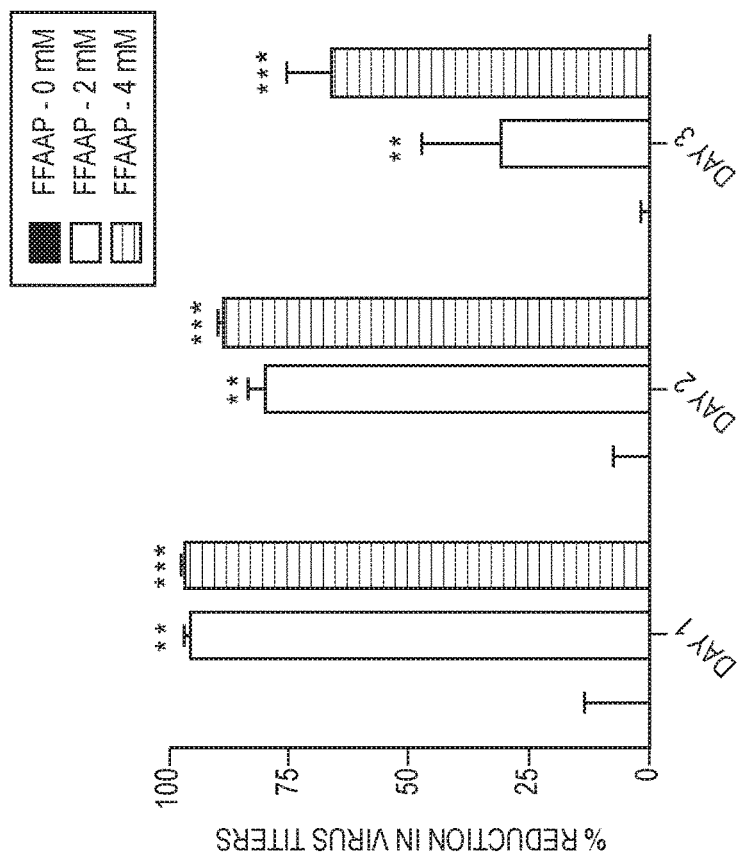
FIGS. 4A and 4B show effect of FFAAP on total intracellular GSH and Zika virus replication in Zika virus infected Vero cells (ZIKV). Vero cells, grown to approximately 90-95% confluence (mid-log phase), were treated with and grown in the presence of increasing concentrations of FFAAP for 3 days. At each time point, medium was discarded and cells were harvested to measure intracellular concentrations of total GSH.
Figure 4A:
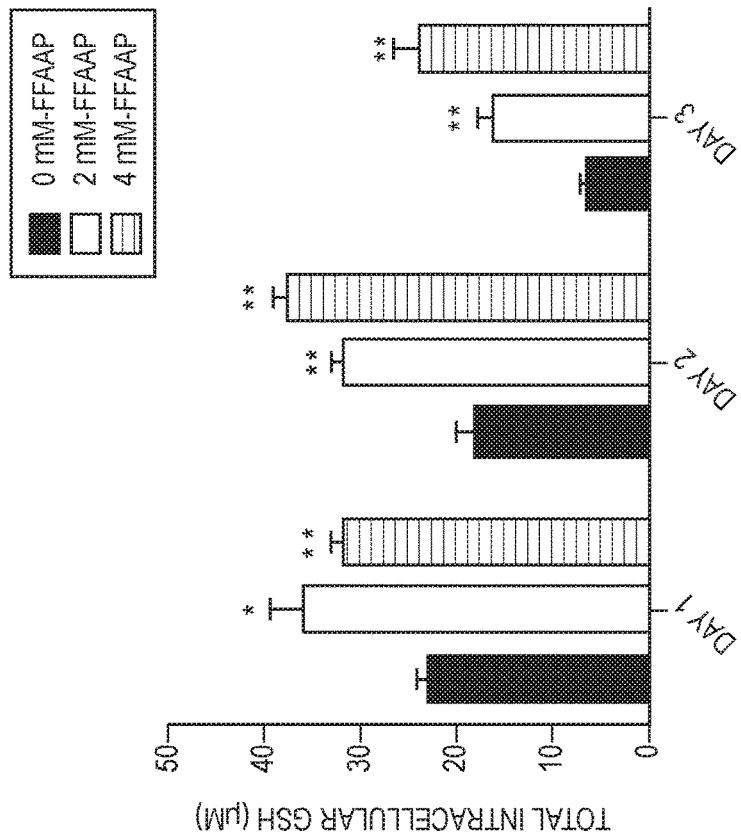
Figure 5A:
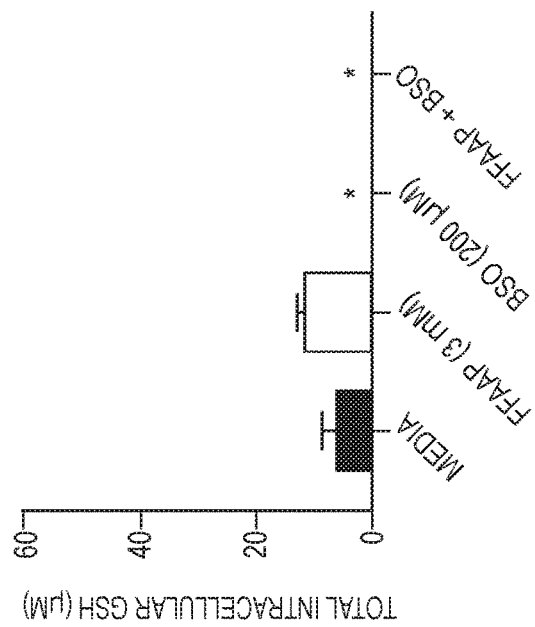
FIG. 5A-5D show effects of inhibition of glutathione biosynthesis on Zika virus replication in Vero cells.
Figure 5B:
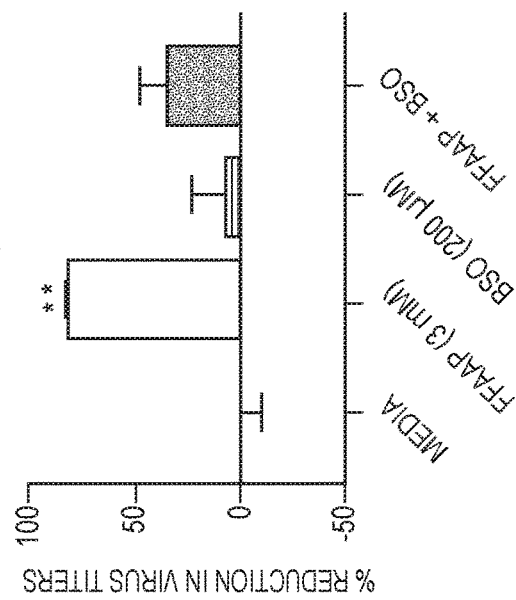
Figure 5C:
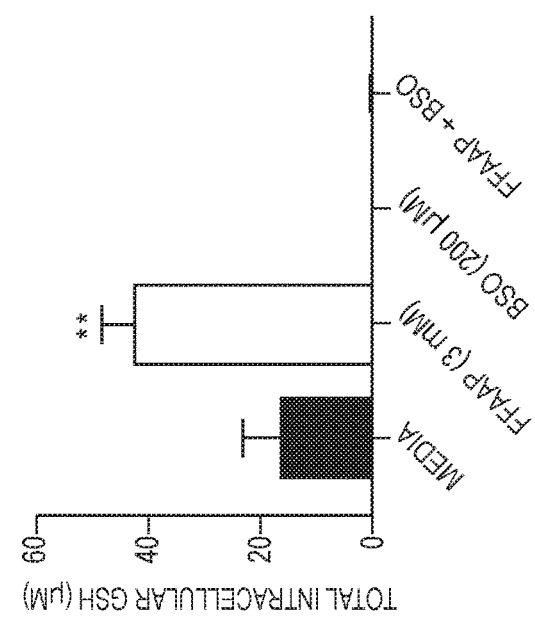
Figure 5D:
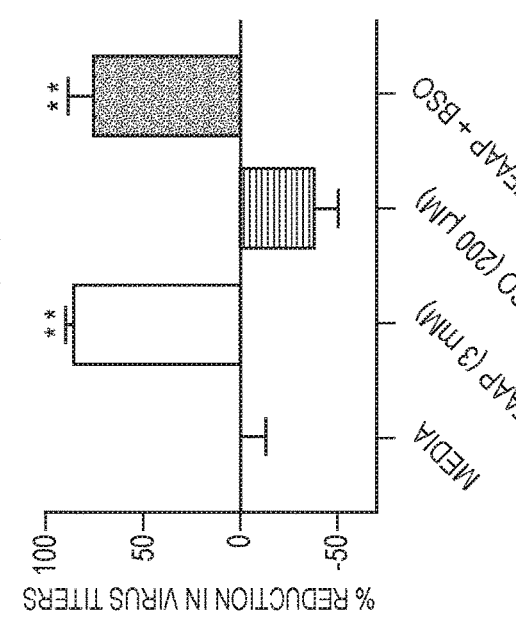
Figure 6A:
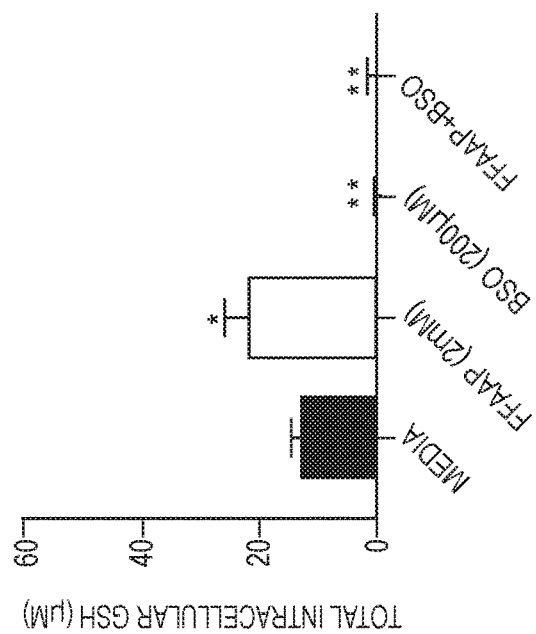
FIGS. 6A-6D show effects of inhibition of glutathione biosynthesis on Zika virus replication in JEG-3 cells.
Figure 6B:
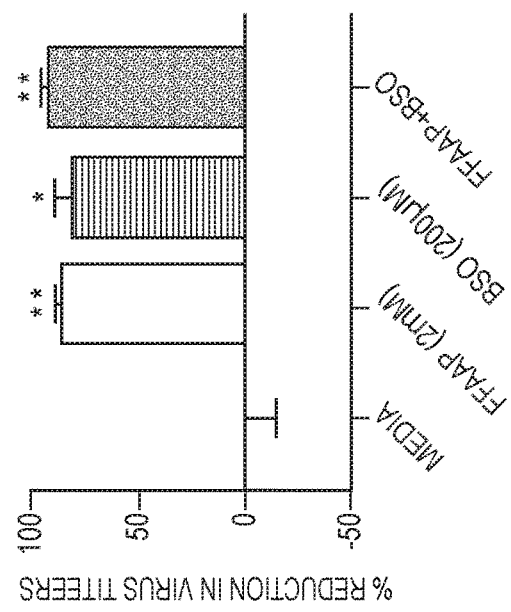
Figure 6C:
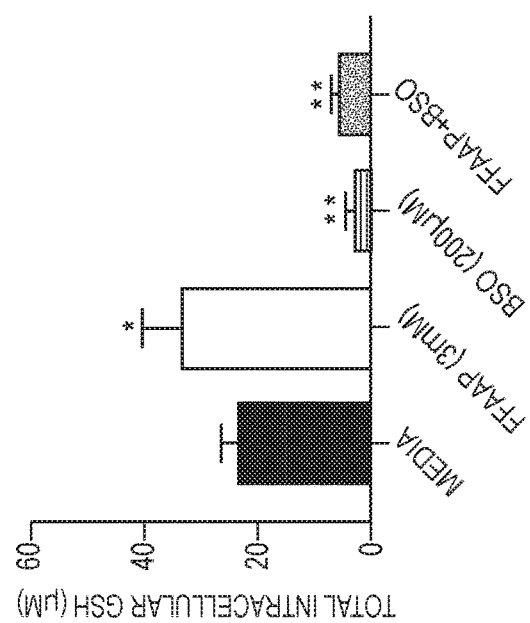
Figure 6D:
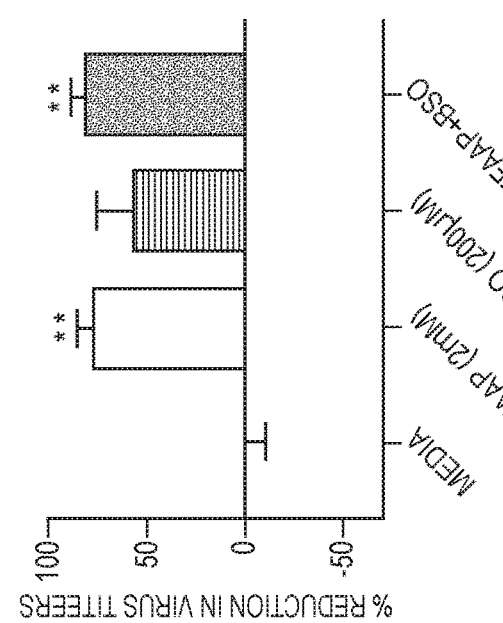
Figure 7A:
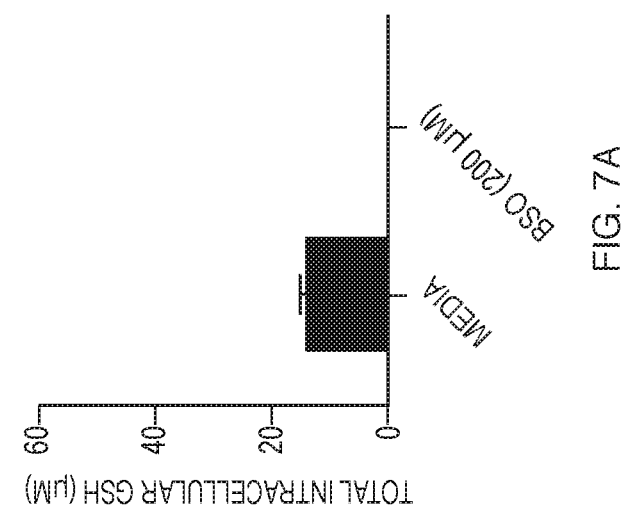
FIGS. 7A-F show total intracellular GSH concentrations in various cells that were treated with BSO, FFAAP, and a combination of BSO and FFAAP at day 0 and day 2.
Figure 7B:
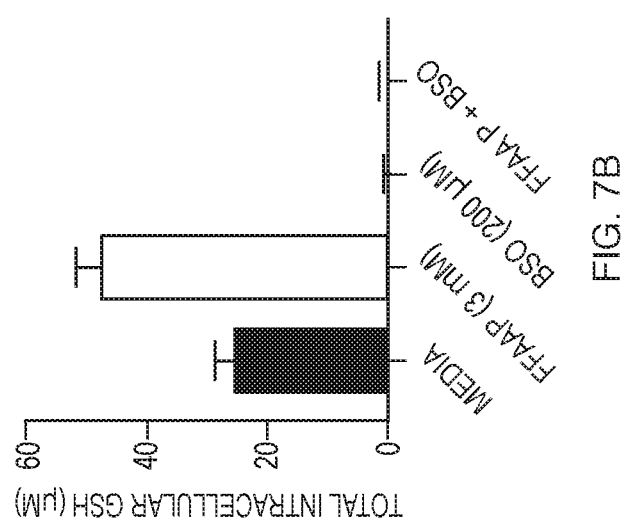
Figure 7C:
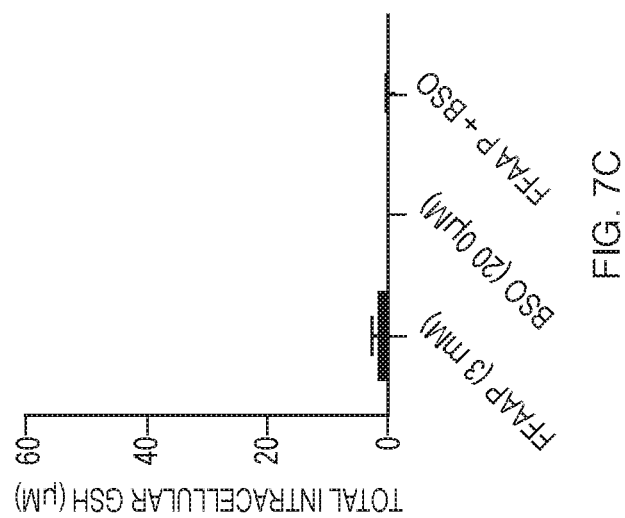
Figure 7F:
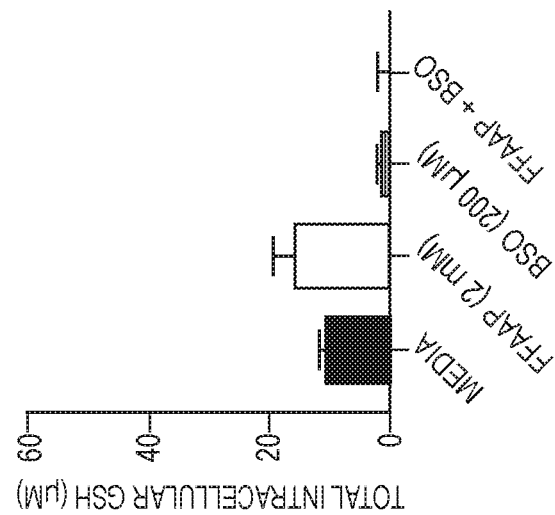
Figure 7E:
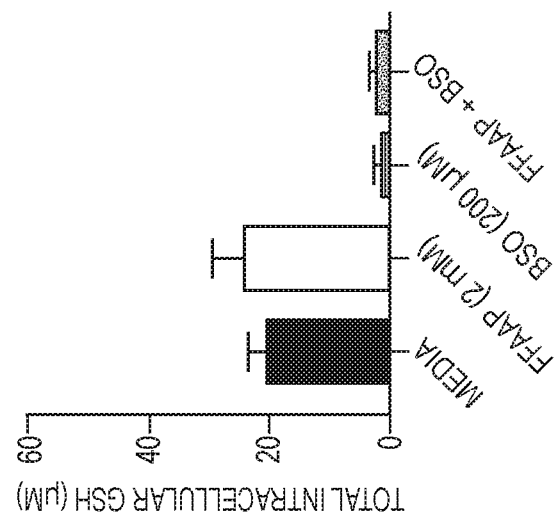
Figure 7D:
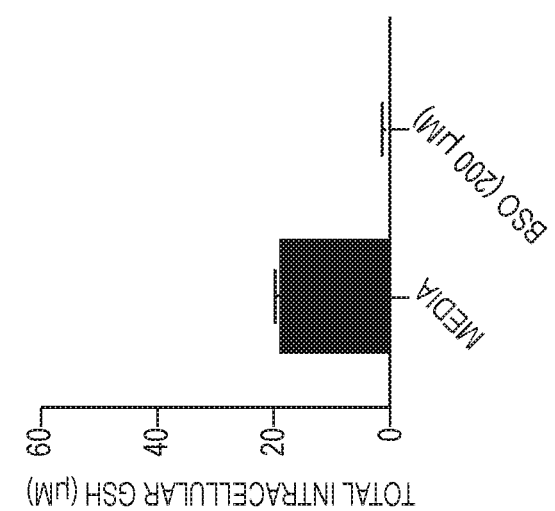

During Zika virus infection of Vero cells, intracellular glutathione diminished rapidly over three DPI in the absence of FFAAP (FIG. 4A). On the other hand, FFAAP-treated infected cells showed marked increases in intracellular glutathione over 72 HPI (three DPI) when compared to untreated cells. At 4 mM concentrations of FFAAP, levels of intracellular glutathione exceeded three standard deviations of the mean of untreated cells. Zika virus yield was reduced significantly in the presence of all concentrations of FFAAP, most notably between 4-6 mM by three DPI (FIG. 4B). The results show greater than 90% reduction in virus levels was observed in Vero cells treated with 2-4 mM FFAAP.

Finally, to validate that intracellular glutathione was responsible for the reduction in Zika virus titers, studies were performed by inhibiting biosynthesis of glutathione in each cell line using buthionine sulfoxime (B SO) (200 µM). Based on the current data, it was hypothesized that B SO-mediated inhibition of glutathione would restore the Zika virus replication to nearly the levels observed in untreated cells. Furthermore, based on the current data, it was rationalized that full restoration would require about 36 hours post infection given the reported half-life of intracellular glutathione of about 36 hours.

Initial studies in Vero cells and JEG-3 cells validated previous findings that with BSO treatment reduced intracellular glutathione levels in to undetectable levels. Moreover, in Zika virus-infected Vero cells, BSO treatment dramatically reduced intracellular levels of glutathione, which was undetectable by 48 hours post BSO-treatment (FIG. 5A and FIG. 5B).

Studies were conducted to further analyze viral replication in Zika-virus infected cells (MOI 0.1), which were treated with BSO at the time of infection or pre-treated for 48 hours prior to infection. Treatment with FFAAP was provided as indicated in FIG. 5C and FIG. 5D. The results in FIG. 5C demonstrates that Zika virus replicates even in Vero cells treated with BSO. However, surprisingly, treatment with FFAAP partially restored inhibition of Zika virus production in Vero cells, especially in cells that had been treated with BSO. Similar results were observed in cells that were pretreated with BSO for 48 hours prior to infection (FIG. 5D). Thus, even in the absence of measurable intracellular glutathione, FFAAP alone reduced Zika virus replication Vero cells.

Similar observations were made when the aforementioned experiments were repeated in JEG-3 cells. Here too, BSO blocked intracellular GSH synthesis in Zika virus infected JEG-3 cells (FIG. 6A and FIG. 6B). Remarkably, in JEG-3 cells, blockage of intracellular biosynthesis of glutathione resulted in inhibition of Zika virus replication, which points to a dependency of Zika virus on intracellular glutathione in JEG-3 cells, which findings are supported by previous reports on West-Nile virus replication in hamster kidney cells (Basu et al., *PLoS Pathog.,* 13(2):e1006240, 2017).

As in the case of Vero cells, Zika virus replication in human JEG-3 cells was significantly inhibited by FFAAP treatment. More specifically, Zika viral replication in JEG-3 cells cultured in the presence of FFAAP and BSO was inhibited by about 90% compared to controls (FIG. 6C and FIG. 6D). Taken together, the results of the aforementioned experiments in Vero and JEG-3 cells indicate that FFAAP may inhibit Zika viral replication by increasing intracellular glutathione levels and/or interacting with viruses directly.

Collectively, these data demonstrate for the first time that FFAAP-treated cells show increases in intracellular levels of glutathione, as evidenced by the levels of intracellular of glutathione shown in each cell-line. See, FIG. 7A-7C (showing results in Vero cells) and FIG. 7D-7F (showing results in JEG-3 cells). Furthermore, FFAAP treatment (2 mM to 4 mM dose) conferred up to 90% reduction of Zika virus yields in the cell-lines that were tested. Particularly, in human JEG-3 cells, the reduction in Zika virus titers was found to be independent of total intracellular GSH concentration.

These data also demonstrate a hitherto unrecognized observation that as Zika virus infection progresses, there is a steady reduction in the biosynthesis of new intracellular glutathione, which can be circumvented and enhanced in the presence of FFAAP. For instance, in Vero cells, FFAAP treatment reduced Zika virus titers by approximately 90% compared to Zika virus titters in untreated cells (controls). Although Zika virus replication in JEG-3 cells depended on intracellular glutathione levels, here too, FFAAP treatment profoundly inhibited replication of the virus.

These studies demonstrate that by increasing biosynthesis of intracellular levels of glutathione beyond that normally observed remarkably impacted infectious Zika virus production in infected mammalian cells. Particularly, experiments were performed to assess Zika virus production in African green monkey cells. The cellular model described herein provides a rapid, efficient way of testing the efficacy of potential therapeutics for controlling Zika virus infection.

Further, the experimental design presented above facilitates assessment of some potential role(s) intracellular glutathione against Zika virus infection. This is the first study to demonstrate that Zika virus rapidly depletes intracellular biosynthesis of glutathione and that increased biosynthesis of intracellular glutathione inhibits Zika virus replication. The effective concentrations of FFAAP that conferred maximum inhibition of Zika virus infection were non-toxic with respect to growth and viability of the cells. A reduction of viral titers by 80% in the presence of 4 mM concentration of FFAAP throughout three DPI demonstrates a surprising efficacy of FFAAP to inhibit Zika virus infection in cells that normally allow productive replication of the virus.

In summary, the results of the study illustrate the protective role of IMMUNE FORMULATION 200® in enhancing intracellular biosynthesis of reduced and oxidized glutathione. Additionally, a significant (about 90%) reduction of virus production via treatment with 2-4 mM concentration of intracellular glutathione demonstrates the efficacy of FFAAP to control Zika virus infection and highlights the therapeutic potential of FFAAP formulation to treat diseases caused by Zika virus in humans and other veterinary animals.

Other embodiments: The preceding examples can be repeated with similar success by substituting the generically or specifically described reactants and/or operating conditions described elsewhere in the specification for those used in the preceding examples.

From the foregoing description, one skilled in the art can easily ascertain the essential characteristics of the methods and, without departing from the spirit and scope thereof, can make various changes and modifications to adapt it to various usages and conditions.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described in the foregoing paragraphs. In addition, the materials, methods, and examples are illustrative only and not intended to be limiting. In case of conflict, the present specification, including definitions, will control.

All United States patents and published or unpublished United States patent applications cited herein are incorporated by reference. All published foreign patents and patent applications cited herein are hereby incorporated by reference. All published references, documents, manuscripts, scientific literature cited herein are hereby incorporated by reference. All identifier and accession numbers pertaining to scientific databases referenced herein (e.g., NCBI, GENBANK, EBI) are hereby incorporated by reference.

We claim:

1. A method for treating Zika viral disease in a subject infected with Zika virus, comprising: administering to the subject, an effective amount of a composition comprising: glycine, L-cystine, a glutamate source selected from the group consisting of glutamine and glutamic acid, and a selenium source.

2. The method of claim 1, comprising administering the composition at an amount effective to reduce infectivity of the Zika virus.

3. The method of claim 2, wherein infectivity of the Zika virus is reduced by at least 40%.

4. The method of claim 1, comprising administering the composition at an amount effective to reduce intracellular replication of the Zika virus.

5. The method of claim 4, wherein the composition is administered at an amount effective to reduce intracellular replication of the Zika virus by at least 25%.

6. The method of claim 4, wherein the composition is administered at an amount effective to reduce intracellular replication of the Zika virus by at least 50%.

7. The method of claim 1, wherein Zika viral disease is Zika fever.

8. The method of claim 1, wherein the selenium source is selected from the group consisting of selenomethionine, selenite, methylselenocysteine and selenium nanoparticles.

9. The method of claim 1, wherein the effective amount of the composition elevates intracellular concentration of glutathione by at least about 25%.

10. The method of claim 1, wherein the effective amount of the composition elevates intracellular concentration of glutathione by at least about 40%.

11. The method of claim 1, wherein administration of the composition is effective to attain an intracellular concentration of glutathione between 10 μM to 50 μM at 24 hours post-administration.

12. The method of claim 1, wherein administration of the composition is effective to attain an intracellular concentration of glutathione between 20 μM to 40 μM at 48 hours post-administration.

13. The method of claim 1, wherein the composition is administered at a dose that is effective to reduce or inhibit depletion of intracellular glutathione levels in Zika virus-infected cells at 24-48 hours post-administration of the composition.

14. The method of claim 1, wherein composition is administered at a dose that is effective to normalize intracellular glutathione levels in Zika virus-infected cells to the intracellular glutathione levels in non-infected cells at 24-48 hours post-administration of the composition.

15. The method of claim 1, wherein the composition is administered about 12 hours to about 96 hours post-infection with the Zika virus.

16. The method of claim 1, wherein the composition is administered about 24 hours to about 72 hours post-infection with the Zika virus.

17. The method of claim 1, wherein the composition is administered about 48 hours post-infection with the Zika virus.

18. The method of claim 1, wherein a Zika virus replication inhibiting amount of the composition is administered.

19. A method for reducing Zika viral load in a biological sample containing cells, comprising contacting the biological sample with an effective amount of a composition comprising glycine, L-cystine, a glutamate source selected from the group consisting of glutamine and glutamic acid, and a selenium source.

20. The method of claim 19, wherein the cells are blood cells, neural cells or epithelial cells.

* * * * *